(12) United States Patent
Yang et al.

(10) Patent No.: US 12,048,754 B2
(45) Date of Patent: Jul. 30, 2024

(54) DENTAL DESENSITIZER

(71) Applicant: Meiyou (Xi'an) Biotechnology Co., Ltd., Xi'an (CN)

(72) Inventors: Peng Yang, Xi'an (CN); Chen Li, Xi'an (CN)

(73) Assignee: MEIYOU (XI'AN) BIOTECHNOLOGY CO., LTD., Xi'an (CN)

( * ) Notice: Subject to any disclaimer, the term of this patent is extended or adjusted under 35 U.S.C. 154(b) by 605 days.

(21) Appl. No.: 17/363,061

(22) Filed: Jun. 30, 2021

(65) Prior Publication Data

US 2021/0322284 A1    Oct. 21, 2021

Related U.S. Application Data

(63) Continuation-in-part of application No. PCT/CN2019/124585, filed on Dec. 11, 2019.

(30) Foreign Application Priority Data

Dec. 30, 2018    (CN) .......................... 201811647134.7

(51) Int. Cl.
*A61K 6/20*    (2020.01)
*A61K 6/60*    (2020.01)
*A61K 6/69*    (2020.01)
*A61K 6/70*    (2020.01)

(52) U.S. Cl.
CPC .................. *A61K 6/20* (2020.01); *A61K 6/60* (2020.01); *A61K 6/69* (2020.01); *A61K 6/70* (2020.01)

(58) Field of Classification Search
CPC ... A61K 6/20; A61K 6/60; A61K 6/69; A61K 6/70; A61K 6/80; A61K 6/831
See application file for complete search history.

*Primary Examiner* — Jessica Worsham
(74) *Attorney, Agent, or Firm* — MATTHIAS SCHOLL P.C.; Matthias Scholl

(57) ABSTRACT

A dental desensitizer, including, by weight: 1-20 parts of a protein modified by polyethylene glycol; 1-10 parts of tris(2-carboxyethyl) phosphine hydrochloride; 1-3 parts of calcium chloride; and 2-20 parts of a pH regulator.

6 Claims, 5 Drawing Sheets

DENTAL DESENSITIZER

CROSS-REFERENCE TO RELATED APPLICATIONS

This application is a continuation-in-part of International Patent Application No. PCT/CN2019/124585 with an international filing date of Dec. 11, 2019, designating the United States, and further claims foreign priority benefits to Chinese Patent Application No. 201811647134.7 filed Dec. 30, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to a dental desensitizer.

Dentin hypersensitivity is dental pain arising from exposed dentin tubules in response to stimuli, typically thermal, evaporative, tactile, osmotic, chemical or electrical. One way to reduce or cure dentin hypersensitivity is to seal the dental tubules. Commercial dental desensitizers can only form a coating on the dentin surface. Under the action of mechanical force, such as brushing and chewing, the coating will be damaged or even fall off.

To seal the dental tubules deeply, an active coating is induced to form in the dental tubules to promote the in-situ remineralization of dentin. However, the formation of the coating is time-consuming, and unstable in acid or base conditions. In addition, in the process of remineralization of dentin, salivary proteins tend to form a film on the dentin, which provides sites for bacterial adhesion, resulting in pulpitis.

SUMMARY

The disclosure provides a dental desensitizer, comprising, by weight: 1-20 parts of a protein modified by polyethylene glycol; 1-10 parts of tris(2-carboxyethyl) phosphine hydrochloride; 1-3 parts of calcium chloride; and 2-20 parts of a pH regulator.

In a class of this embodiment, the dental desensitizer comprises, by weight: 4-10 parts of a protein modified by polyethylene glycol; 2-6 parts of tris(2-carboxyethyl) phosphine hydrochloride; 1-2 parts of calcium chloride; and 6-10 parts of a pH regulator.

In a class of this embodiment, the protein is selected from the group consisting of lysozyme, bovine serum protein, insulin, α-lactalbumin, or a mixture thereof.

In a class of this embodiment, a number-average molecular weight of polyethylene glycol is in the range of 200 to 20000.

In a class of this embodiment, the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

The method for using the tooth desensitizer of the disclosure is as follows: adding the dental desensitizer to deionized water, and stirring to fully dissolve the raw materials of the dental desensitizer, to yield a 1-400 mg/mL desensitizer solution; controlling the pH of the desensitizer solution to be 7-7.5; evenly coating the dentin with the desensitizer solution using a cotton swab, or immersing the dentin in the desensitizer solution for 2-5 minutes.

In vitro and animal experiments show that the desensitizer solution can be deeply coated in the dentin tubules. A large number of calcium ions in the desensitizer solution are combined with the protein. When the protein is attached to the dentin surface, the remineralization of dentin tubules is induced thereby deeply sealing the dentin tubules. The sealing depth is up to 40 μm. In addition, the coating of the desensitizer solution can effectively resist the adhesion of bacteria and prevent the formation of the biofilm, thus preventing the occurrence of dental caries and pulpitis.

The following advantages are associated with the dental desensitizer of the disclosure:

1. The main components of the dental desensitizer are protein, which is non-toxic and nonirritating, is biocompatible, and can be stably preserved and convenient for subsequent use.

2. When in use, the dental desensitizer solution is coated on the tooth slice or the tooth slice is immersed in the dental desensitizer solution, which is easy to operate.

3. Different from the traditional tooth desensitizer which directly covers the surface of dental tubules, the dental desensitizer of the disclosure can form a nanometer coating inside the dental tubules, induce remineralization of dentin in saliva environment, and seal the dental tubules from the inside.

4. The coating formed by the dental desensitizer of the disclosure is antibacterial, can prevent bacterial adhesion and inhibit the formation of the biofilm on dentin.

5. The dental desensitizer of the disclosure can resist the physical effects of brushing, ultrasonic cleaning, etc. after sealing the dental tubules.

DETAILED DESCRIPTION

Figure 1:
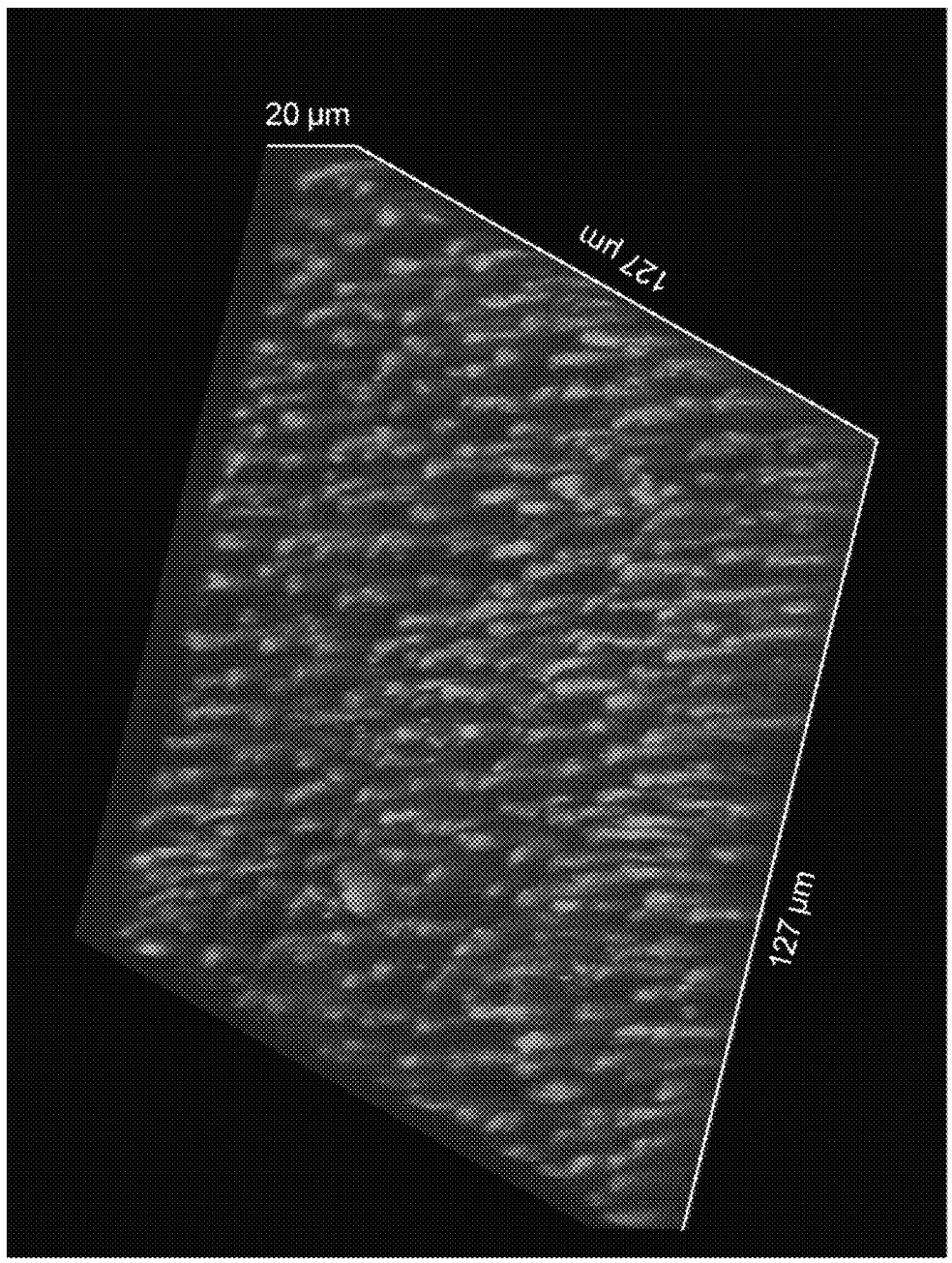
FIG. 1 is a Confocal Laser Scanning Microscope (CLSM) 3D image of a dental desensitizer of the disclosure in a dentine tubule.

To further illustrate, embodiments detailing a dental desensitizer are described below. It should be noted that the following embodiments are intended to describe and not to limit the disclosure.

Example 1

40 mg of lysozyme modified by polyethylene glycol, 10 mg of tris(2-carboxyethyl) phosphine hydrochloride, 10 mg of calcium chloride, and 60 mg of sodium bicarbonate were evenly mixed to yield a dental desensitizer.

Example 2

50 mg of lysozyme modified by polyethylene glycol, 15 mg of tris(2-carboxyethyl) phosphine hydrochloride, 15 mg of calcium chloride, and 70 mg of sodium carbonate were evenly mixed to yield a dental desensitizer.

Example 3

60 mg of lysozyme modified by polyethylene glycol, 20 mg of tris(2-carboxyethyl) phosphine hydrochloride, 10 mg of calcium chloride, and 80 mg of sodium carbonate were evenly mixed to yield a dental desensitizer.

Example 4

10 mg of lysozyme modified by polyethylene glycol, 60 mg of tris(2-carboxyethyl) phosphine hydrochloride, 20 mg of calcium chloride, and 20 mg of sodium bicarbonate were evenly mixed to yield a dental desensitizer.

Example 5

100 mg of lysozyme modified by polyethylene glycol, 60 mg of tris(2-carboxyethyl) phosphine hydrochloride, 30 mg of calcium chloride, and 100 mg of sodium bicarbonate were evenly mixed to yield a dental desensitizer.

Example 6

150 mg of lysozyme modified by polyethylene glycol, 100 mg of tris(2-carboxyethyl) phosphine hydrochloride, 20 mg of calcium chloride, and 100 mg of sodium bicarbonate were evenly mixed to yield a dental desensitizer.

Example 7

200 mg of lysozyme modified by polyethylene glycol, 100 mg of tris(2-carboxyethyl) phosphine hydrochloride, 10 mg of calcium chloride, and 200 mg of sodium bicarbonate were evenly mixed to yield a dental desensitizer.

The lysozyme modified by polyethylene glycol in Examples 1-7 were prepared as follows: 10 g of polyethylene glycol 2000 and 5 g of N, N'-disuccinimide carbonate were dissolved in 30 mL of trichloromethane, and then 0.61 g of triethylamine was added and magnetically stirred for 8 hours at room temperature. Thereafter, glacial ether as a precipitant was added to the solution, whereby succinimide terminated polyethylene glycol was obtained. 1 g of succinimide terminated polyethylene glycol and 0.14 g of lysozyme were dissolved in 20 mL of tris(hydroxymethyl) aminomethane buffer of tris (2-carboxyethyl) phosphine having a pH of 7.5. The mixed solution was stirred for 8 hours at room temperature, dialyzed, and lyophilized, to yield lysozyme modified by polyethylene glycol.

Optionally, following the abovementioned preparation method of lysozyme modified by polyethylene glycol, polyethylene glycol with other molecular weight can also be used for the pegylation of lysozyme.

Still optionally, following the abovementioned preparation method of lysozyme modified by polyethylene glycol, polyethylene glycol with various molecular weights can also be used for the pegylation of bovine serum protein, insulin, α-lactalbumin, etc. to yield pegylated bovine serum protein, pegylated insulin, and pegylated α-lactalbumin.

To illustrate the technical effect of the dental desensitizer, 60 mg of the dental desensitizer obtained in Example 1 was added to 10 mL of deionized water, shaken for dissolution, to yield a 6 mg/mL desensitizer solution having a pH of 7.2. The performance of the desensitizer solution was tested as follows:

1. Test of Coating Performance of Dental Desensitizer

Fresh extracted teeth without caries and wear were collected, washed, cut into 1 mm thick dentin slices by a slow saw, cooled by flowing water, and then processed into 5 mm×5 mm×5 mm dentin samples by a polishing machine. The dentin samples were rinsed with EDTA solution and NaClO aqueous solution alternately for 20 seconds for experiments in vitro.

The dentin samples were soaked in the desensitizer solution for 2 minutes at room temperature. The dental desensitizer can specifically bind to the fluorescent dye thiophanate T (THT), which can be manifested by CLSM. The results show that the dental desensitizer is deeply coated in the DTs (as shown in FIG. 1).

2. Anti-Biofilm Test of Dental Desensitizer

The tooth slices coated with the dental desensitizer in Test 1 were placed in a 24-well plate, and 1 mL of *Streptococcus mutans* suspension ($10^9$ cells/mL) containing culture medium was added. The tooth slices were cultured at 37° C. for 24 hours, and then washed with deionized water. The growth of biofilm was observed. The teeth without the dental desensitizer were used as a control group.

Figure 2:
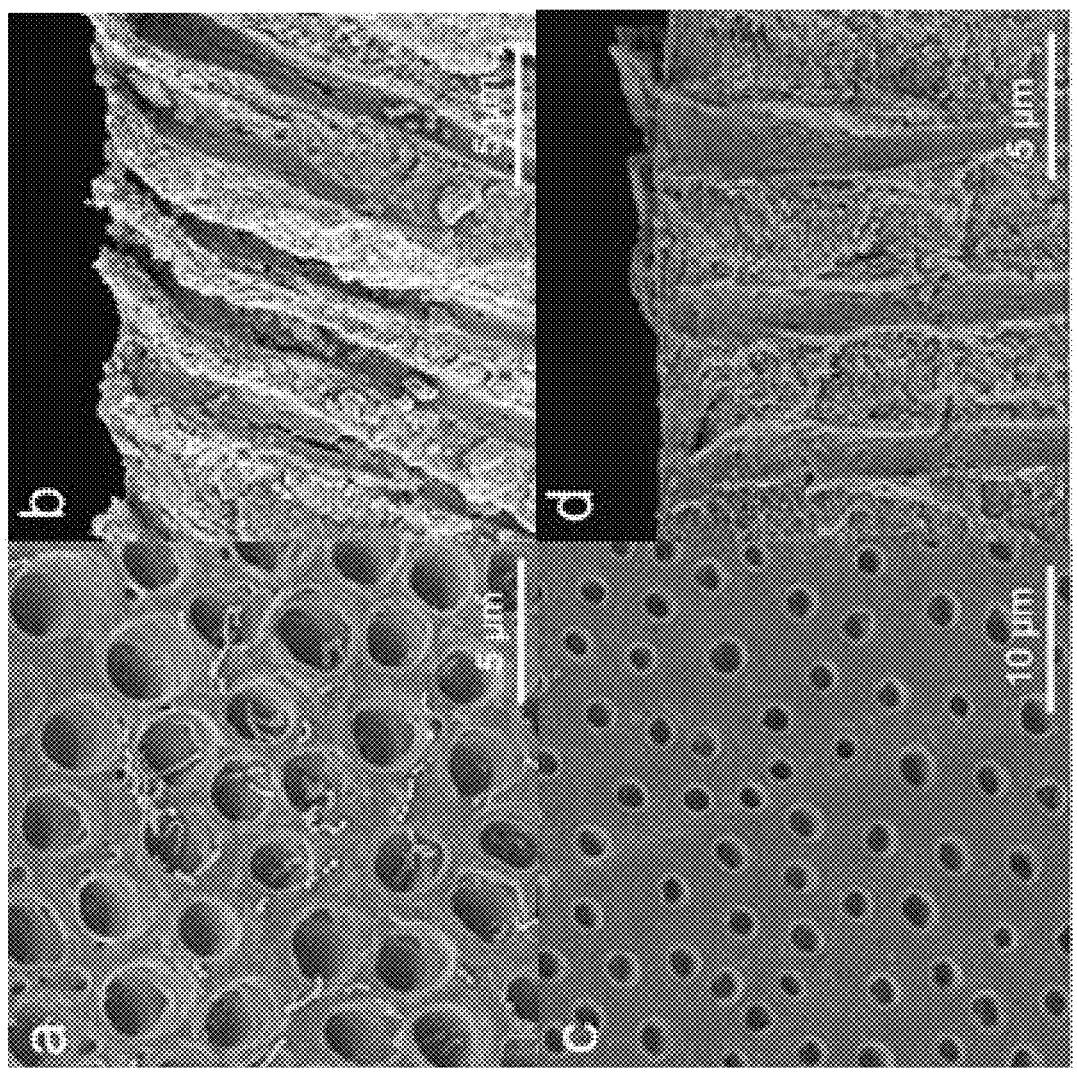
FIG. 2 shows Scanning Electron Microscope (SEM) images of dentine tubules (DTs): a: top surface of bare dentine tubules; b: cross-section of bare DTs; c: top surface of DTs coated with the dental desensitizer; d: cross-section of DTs coated with the dental desensitizer.
Figure 3:
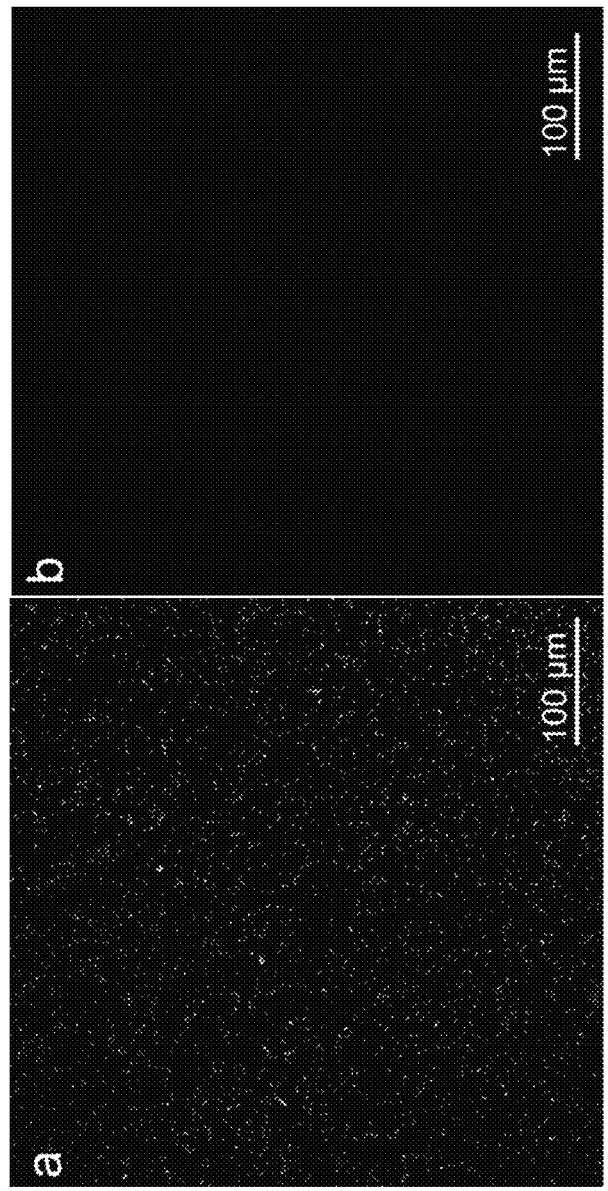
FIG. 3 shows the Biofilm (S. mutans) formation on bare dentin (a) and dental desensitizer coated dentin (b)

It can be seen from the SEM of FIG. 2 that there were a large number of bacteria adhering on the tooth piece in the control group. It can also be seen from the cross-section that bacteria penetrated into the interior of dental tubules, causing pulpitis and other diseases. However, there was almost no bacteria adhesion on the dental piece coated with the dental desensitizer, and no bacteria entered into the dental tubules. In addition, it can be seen from the laser scanning confocal microscope photos that there were a large number of bacteria on the blank tooth slices stained with cell stain, while there was no bacterial adhesion on the tooth slices coated with the dental desensitizer (see FIG. 3). The above tests prove that the desensitizer can be coated on the dentin, and can resist the formation of the biofilm on the dentin.

3. In Vitro Test of the Performance of Dental Desensitizer in Sealing Dental Tubules The tooth slices coated with the dental desensitizer in test 1 were placed in a 24-well plate, and 1 mL of simulated saliva was added, and placed in a 37° C. incubator. The simulated saliva was refreshed every 12 hours. After 7 days, the teeth were taken out and the sealing condition of dental tubules was observed. The teeth without the dental desensitizer were used as a control group.

Figure 4:
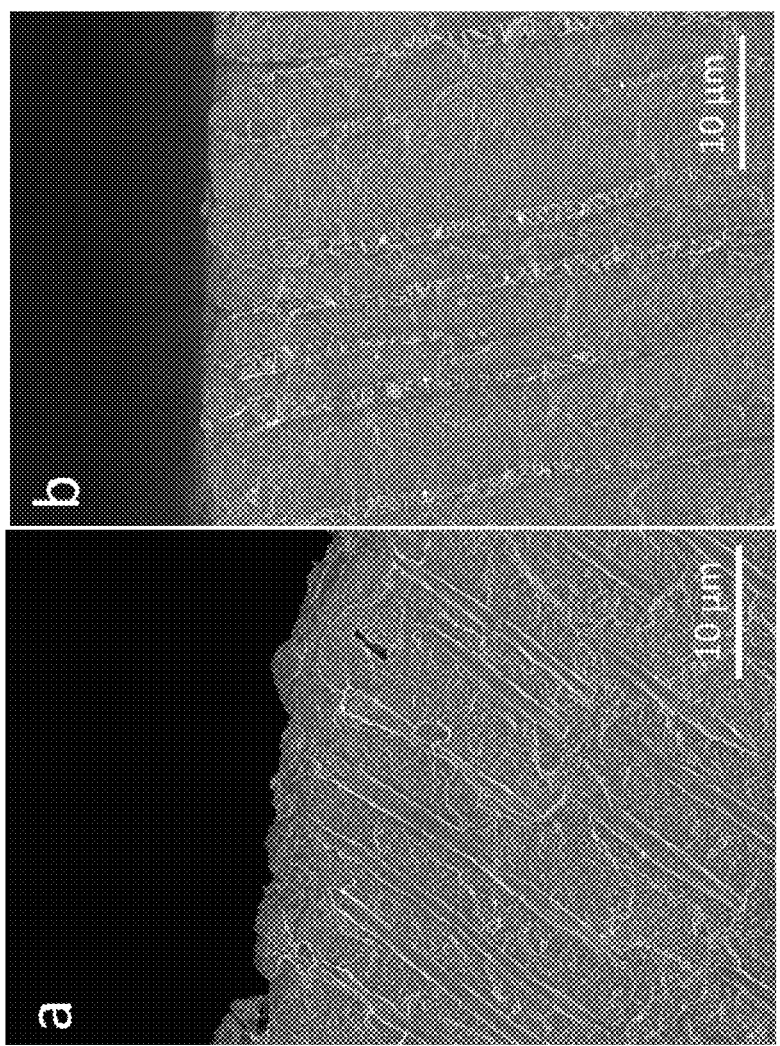
FIG. 4 shows SEM images of DTs; a: cross-section of bare DTs; b: cross-section of DTs coated with the dental desensitizer.

As shown in FIG. 4, the tubules of the teeth coated with the dental desensitizer were sealed by remineralized crystals, and the sealing depth was up to 40 μm. The EDX spectrum analysis showed that the remineralized crystal was hydroxyapatite. However, in the control group, there was no mineralized crystal in the dental tubules, and the dental tubules were exposed. The test shows that the dental desensitizer can be coated inside the dental tubules to resist the formation of the biofilm on the dentin surface, and induce the remineralization of hydroxyapatite in the simulated saliva environment, so as to deeply seal the dental tubules and achieve the effect of long-term desensitization of the teeth.

4. Animal Experiment Test of the Performance of Dental Desensitizer in Sealing the Dental Tubules The tooth slices coated with the dental desensitizer in Test 1 were fixed in the oral cavity of mice (8 weeks old, weighing 220-300 g), and were taken out for observation after 14 days. The teeth without the dental desensitizer were used as a control group.

Figure 5:
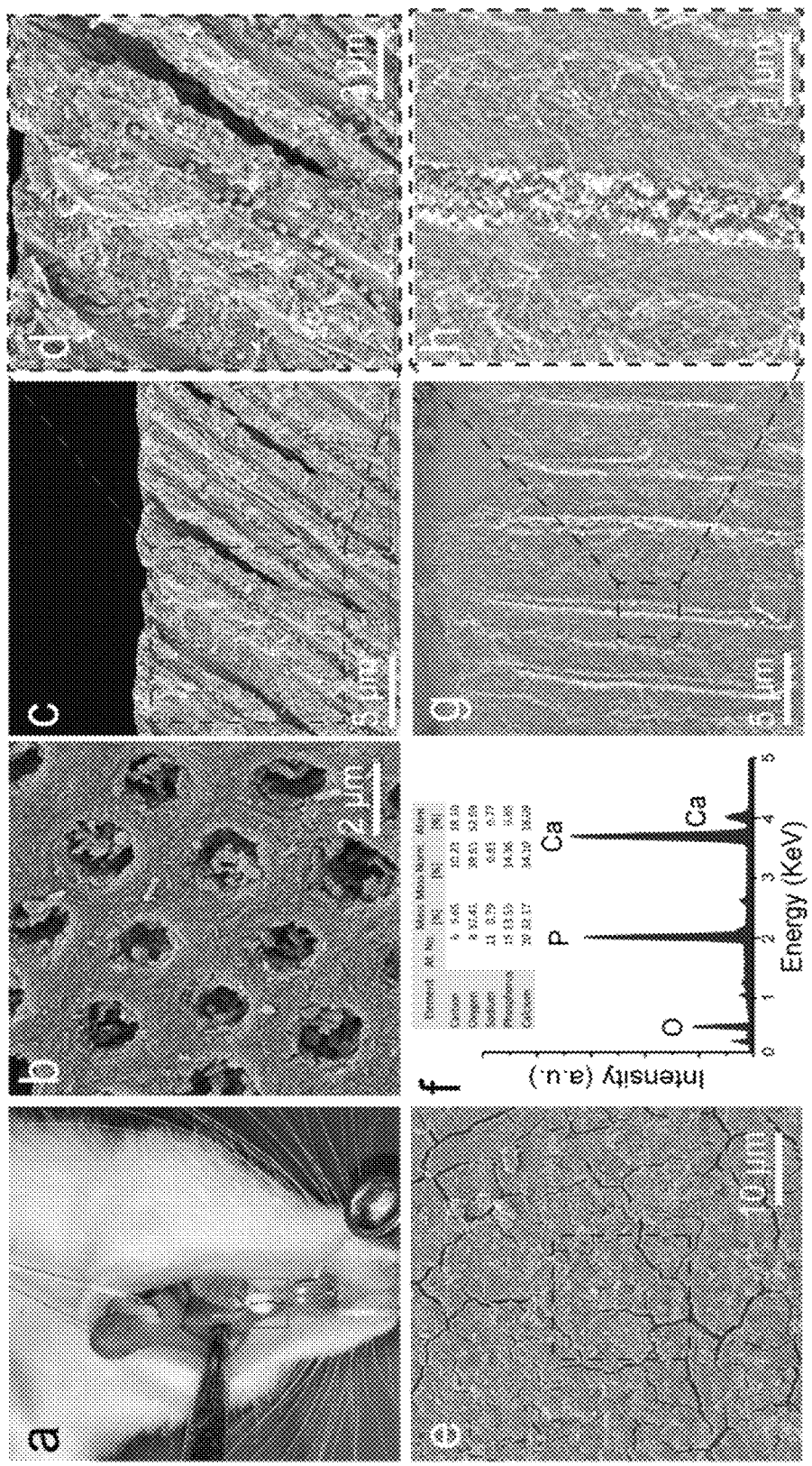
FIG. 5 shows in vivo occlusion of DTs in animal experiments. a: Dentin disk was fixed in the oral cavity of rats; b: SEM images of bare dentin after 14 days incubation in oral cavity of rat; c and d: Cross-section SEM image of bare dentin after 14 days incubation and its high-resolution image; e: SEM images of dental desensitizer coated dentin after 14 days incubation in oral cavity of rat; f: EDX spectrum of dental desensitizer coated dentin after 14 days incubation in the oral cavity of rat; g and h: Cross-section SEM image of dental desensitizer coated dentin after 14 days incubation and its high-resolution image.

As shown in FIG. 5, no mineralized layer was formed on the tooth slices of the control group, and bacteria proliferated in the dental tubules. The cross-section view also showed that bacteria penetrated into the dental tubules. However, in the tooth slices coated with the dental desensitizer, the mineralized layer completely covered the dental tubules. In addition, the cross-sectional view showed that the interior of the dental tubules was sealed and no bacteria grew therein. The animal experiment test shows that the dental desensitizer can be coated inside the dental tubules to resist the formation of the biofilm on the dentin surface, and induce the remineralization of hydroxyapatite in the simulated saliva environment, so as to deeply seal the dental tubules and achieve the effect of long-term desensitization of the teeth.

It will be obvious to those skilled in the art that changes and modifications may be made, and therefore, the aim in the appended claims is to cover all such changes and modifications.

What is claimed is:

1. A dental desensitizer, comprising, by weight:
   1-20 parts of a protein modified by polyethylene glycol;
   1-10 parts of tris(2-carboxyethyl) phosphine hydrochloride;
   1-3 parts of calcium chloride; and
   2-20 parts of a pH regulator, wherein the protein is selected from the group consisting of lysozyme, bovine serum protein, insulin, α-lactalbumin, or a mixture thereof.

2. The dental desensitizer of claim 1, comprising by weight:
   4-10 parts of the protein modified by polyethylene glycol;
   1-2 parts of tris(2-carboxyethyl) phosphine hydrochloride;
   1-2 parts of calcium chloride; and
   6-10 parts of the pH regulator.

3. The dental desensitizer of claim 1, wherein a number-average molecular weight of polyethylene glycol is in the range of 200 to 20000.

4. The dental desensitizer of claim 2, wherein a number-average molecular weight of polyethylene glycol is in the range of 200 to 20000.

5. The dental desensitizer of claim 1, wherein the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

6. The dental desensitizer of claim 2, wherein the pH regulator is sodium carbonate, sodium bicarbonate, potassium carbonate, potassium bicarbonate, dipotassium hydrogen phosphate, dipotassium hydrogen phosphate, sodium benzoate, sodium citrate, or a mixture thereof.

* * * * *